(12) United States Patent
Hayashi et al.

(10) Patent No.: US 9,945,773 B2
(45) Date of Patent: Apr. 17, 2018

(54) FLOW CELL AND LIQUID FEED SYSTEM (71) Applicant: NIPPON TELEGRAPH AND TELEPHONE CORPORATION, Tokyo (JP)

(72) Inventors: Katsuyoshi Hayashi, Tokyo (JP); Yuzuru Iwasaki, Tokyo (JP); Suzuyo Inoue, Tokyo (JP); Nobuaki Matsuura, Tokyo (JP); Tsutomu Horiuchi, Tokyo (JP); Emi Tamechika, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 67 days.

(21) Appl. No.: 15/115,881

(22) PCT Filed: Feb. 2, 2015

(86) PCT No.: PCT/JP2015/052825
§ 371 (c)(1),
(2) Date: Aug. 1, 2016

(87) PCT Pub. No.: WO2015/119072
PCT Pub. Date: Aug. 13, 2015

(65) Prior Publication Data
US 2017/0010205 A1 Jan. 12, 2017

(30) Foreign Application Priority Data
Feb. 5, 2014 (JP) .................................. 2014-020091

(51) Int. Cl.
*G01N 21/05* (2006.01)
*B01L 3/00* (2006.01)
*G01N 35/10* (2006.01)

(52) U.S. Cl.
CPC .............. *G01N 21/05* (2013.01); *B01L 3/502* (2013.01); *B01L 3/50273* (2013.01);
(Continued)

(58) Field of Classification Search
CPC ..... G01N 21/03–21/09; G01N 35/1095; B01L 2300/0848; B01L 2300/0877;
(Continued)

(56) References Cited

U.S. PATENT DOCUMENTS 5,599,502 A * 2/1997 Miyazaki .......... B01L 3/502715
356/410
6,401,769 B1 * 6/2002 Backes ................ B01J 19/0046
141/31

(Continued)

FOREIGN PATENT DOCUMENTS

JP H06-010900 A 1/1994
JP H10-160658 A 6/1998
(Continued)

OTHER PUBLICATIONS

Horiuchi et al., "Passive Fluidic Chip Composed of Integrated Vertical Capillary Tubes Developed for On-Site SPR Immunoassay Analysis Targeting Real Samples", Sensors 12, No. 6 pp. 7095-7108 (2012).

(Continued)

*Primary Examiner* — Kara E Geisel
*Assistant Examiner* — Violeta A Prieto
(74) *Attorney, Agent, or Firm* — Womble Bond Dickinson (US) LLP (57) ABSTRACT A flow cell (2) includes a plate-shaped body 21 that is almost rectangular in a plan view, an introduction portion (22) that is made of a concave portion formed in the upper surface of the body (21), a channel (23) that is formed inside the body (21) and has one end connected to the lower end of the (Continued)

introduction portion (22), and a delivery portion (24) that is made of a concave portion formed in the body (21) and has the lower end connected to the other end of the channel (23). The introduction portion (22) is formed to cause the meniscus of a liquid introduced from an opening to apply, to the liquid, a positive pressure or a negative pressure whose absolute value is smaller than that of a negative pressure applied to the liquid introduced into the channel (23) by the meniscus of the liquid. The channel (23) is formed to cause the meniscus of the liquid introduced into the channel (23) to apply a negative pressure to the liquid. This invention provides a flow cell and a liquid feed system capable of more easily controlling feed of a trace amount of liquid.

1 Claim, 7 Drawing Sheets

(52) U.S. Cl.
CPC .. *G01N 35/1095* (2013.01); *B01L 2300/0848* (2013.01); *B01L 2300/0877* (2013.01); *B01L 2400/0406* (2013.01); *B01L 2400/049* (2013.01); *B01L 2400/0487* (2013.01)

(58) Field of Classification Search
CPC ..... B01L 2400/0406; B01L 2400/0487; B01L 2400/049; B01L 3/502; B01L 3/50273
See application file for complete search history.

(56) References Cited

U.S. PATENT DOCUMENTS

2006/0119852 A1* 6/2006 Shimizu ................. G01N 21/05
356/445

2010/0288368 A1* 11/2010 Beebe ................. B01L 3/50273
137/12
2012/0051947 A1* 3/2012 Beebe ................. B01L 3/50273
417/53

FOREIGN PATENT DOCUMENTS

| JP | 2010-531971 A | 9/2010 |
|---|---|---|
| JP | 4853927 B | 11/2011 |
| JP | 4897054 B | 1/2012 |
| JP | 4987088 B | 5/2012 |
| JP | 5042371 B | 7/2012 |
| WO | WO 2009/145172 A1 | 5/2009 |

OTHER PUBLICATIONS

Walker et al., "A passive pumping method for microfluidic devices", Lab Chip 2 pp. 131-134 (2002).

Kim et al, "Plasma extraction in a capillary-driven microfluidic device using surfactant-added poly (dimethylsiloxane)", Sensors and Actuators B 145, pp. 861-868 (2010).

Kim et al., "Preprogrammed capillarity to passively control system-level sequential and parallel microfluidic flows", Lab Chip, vol. 13, pp. 2091-2098 (2013).

Horiuchi et al., "Cooperative Suction by Vertical Capillary Array Pump for Controlling Flow Profiles of Microfluidic Sensor Chips", Sensors, vol. 12, pp. 14053-14067 (2012).

Li et al., "A Capillary-Pressure-Based Air Pump for Nanoliter Liquid Handling in Microfluidic Devices", Proceedings of the 15th International conference on Miniaturized Systems for Chemistry and Life Science, pp. 918-920 (2011).

Lynn et al., "Passive microfluidic pumping using coupled capillary evaporation effects", Lab Chip, vol. 9, pp. 3422-3429 (2009).

* cited by examiner

FLOW CELL AND LIQUID FEED SYSTEM

TECHNICAL FIELD

The present invention relates to a flow cell and a liquid feed system.

BACKGROUND ART

Various kinds of measurement are performed in clinical examinations or examinations in the biochemical field. At this time, the amount of a sample solution to be measured is often very small. Hence, there are proposed technologies such as micro TAS (Total Analysis Systems) and Lab on a Chip, in which measurement is conducted at high sensitivity by controlling the flow of a trace amount of liquid using a small chip.

In such technologies, a simple measurement method such as fluorometry, absorptiometry, electrochemical measurement, QCM (Quartz Crystal Microbalance) measurement, ATR (Attenuated Total Reflection) measurement, or SPR (Surface Plasmon Resonance) measurement is employed in many cases. In particular, the SPR measurement does not need specimen liquid labeling for detection, and can directly detect an antigen-antibody reaction or DNA combination and also simplify the measurement procedure (for example, see patent literatures 1 to 3 and non-patent literature 1). Additionally, in the SPR measurement, since the measurement area can be linear or planar, the flow velocity between two points can be measured by measuring the time difference in the refractive index change between the two points (for example, see patent literature 4).

In these measurement techniques, a sample cell capable of holding a sample solution is used. A trace amount of sample solution is supplied to the sample cell and fed, in the sample cell, to a detection portion that performs measurement. This makes it possible to conduct measurement at higher sensitivity and higher efficiency without lowering the concentration of a specimen such as DNA or an antibody dissolved or dispersed in the sample solution. The sample cell that feeds the sample solution to the detection portion is called a flow cell.

Various kinds of methods are proposed as methods of transferring a trace amount of sample solution in a flow cell. For example, there is a method of transferring a sample solution to a channel formed in a flow cell by applying a pressure from outside using a syringe pump or the like. There also exist a method of transferring a sample solution using an electrostatic force, an electrowetting method, a method of transferring a sample solution using a volume change or bubble generation by heating, and a method using an electroosmotic flow.

Also recently proposed is a method of transferring a sample solution by forming, in a flow cell, a region serving as a channel or pump capable of manifesting capillarity for the sample solution (for example, see patent literature 2). For this method, a flow cell is proposed in which a supply portion including an introduction port to introduce a sample solution, a transfer portion including a capillary pump that sucks the introduced sample solution, and a channel for measurement provided between the introduction port and the capillary pump are formed on a line along the planar direction of a plate-shaped flow cell. In this flow cell, when the sample solution is supplied to the introduction port, the sample solution enters from the introduction port and reaches the capillary pump via the channel. The sample solution is sucked by the capillary pump and continuously flows through the channel. There is also proposed a method of forming droplets of different radii at the two ends of a channel and transferring the liquid by the difference between the magnitudes of surface tensions generated on the droplets (for example, see non-patent literature 2).

The liquid feed method using the capillary force is called a passive pump because no external driving force is needed. A flow cell having the passive pump does not need a peripheral device for liquid feed and is therefore advantageous in on-site measurement such as point of care. Particularly, in the flow cell described in patent literature 1, a specimen liquid does not flow out of the flow cell. Hence, the biohazardous effect on the operator is small, and wastes associated with measurement can be reduced. In addition, one flow cell is used only once in measurement and then discarded. It is therefore possible to suppress measurement errors such as cross contamination.

Since a manufacturing method based on lithography is used, silicon, quartz, a glass wafer, or the like is used the material of the flow cell. As a bonding method for forming the flow cell, a method using heating and fusing, anodic bonding, bonding by hydrofluoric acid, or the like is used.

To cause the flow cell to function as a biosensor, a biomaterial is immobilized in the flow cell. However, the biomaterial has a low resistance to a high temperature, strong acid, strong alkali, and organic solvent. It is therefore difficult to make the flow cell function as a biosensor if it is manufactured using the above-described bonding method after the biomaterial is immobilized.

Studies have recently been conducted on using polydimethylsiloxane (to be referred to as "PDMS" hereinafter) as the material of a flow cell. This is because PDMS has a strong self-adhesive force to a glass or silicon substrate and does not need a bonding process, and a flow cell can easily be manufactured only placing the PDMS on the substrate. In addition, PDMS is hydrophobic because its contact angle to an aqueous solution is 90° or more. In liquid feed using the surface tension of a droplet, the hydrophobicity is advantageous in forming the droplet. However, to introduce a solution serving as priming water in advance, forcible liquid feed using a pipette or the like is needed as preconditioning. This is because even if the substrate that forms the channel is hydrophilic, the remaining surfaces are made of the hydrophobic PDMS, and an aqueous solution cannot be introduced without pressurization from outside.

As is apparent from this, it is difficult to implement, only by PDMS, the passive pump using the capillary force as the driving force. For this reason, a reagent is applied to the PDMS surface to attain hydrophilicity. However, the hydrophilicity is lost as time elapses. Studies have been conducted on adding a modifying agent to the PDMS itself to make the PDMS itself hydrophilic and manufacturing a flow cell for blood test (for example, see non-patent literature 3).

The above-described flow cell is of a disposable type aiming at easy measurement on site. On the other hand, there also exists a demand to collect many specimen liquids to an analysis center or the like and analyze an enormous number of specimens. In this case, the environment permits operators to use sufficient power, water, and drug solutions, and there are few constraints of the size of the measurement device. Hence, the measurement cost can be reduced by repetitive measurement in which instead of using a disposable flow cell, after a specimen liquid is fed to the channel, water or a cleaning fluid is subsequently fed to clean the channel, and the next specimen liquid is then fed.

To implement the repetitive measurement, there is proposed a flow cell including a supply portion with an introduction port to introduce a sample solution, a discharge portion with a delivery port to deliver the sample solution, and a channel for measurement provided between the supply portion and the discharge portion. In this flow cell, liquid feed is generally controlled by a pump (for example, see patent literatures 5 and 6). More specifically, a negative pressure is applied to the pump connected to the delivery port to suck a specimen liquid or cleaning fluid supplied to the supply portion, thereby feeding the liquid.

In a case in which repetitive measurement is performed using this flow cell, for example, if the negative pressure is continuously applied to completely suck the liquid in the channel or delivery portion, it is difficult to suck a liquid to be measured next that is supplied to the supply portion because a gas exists in the channel or delivery portion. In this case, priming water needs to be supplied to the flow cell to fill the channel or delivery portion with the liquid, resulting in an increase in time. In the repetitive measurement, the operation of the pump is controlled to attain a state in which the liquid stays in the channel and the delivery portion. For example, the pump is stopped when the liquid in the introduction portion completely flows to the channel, thereby attaining the state in which the liquid stays in the channel and the delivery portion.

Such repetitive measurement is effective in, for example, blood coagulation measurement. In recent years, life-style related diseases caused by a Western dietary life, lack of exercise, accumulation of stress, the progress of aging, and the like have become a serial social problem. An example of a disease caused by the life-style related diseases is a thrombosis. The thrombosis is strongly correlated with a myocardial infarction. Hence, it will be more important to do blood coagulation measurement in a periodic blood test in the future.

RELATED ART LITERATURE

Patent Literature

Patent Literature 1: Japanese Patent No. 04987088
Patent Literature 2: Japanese Patent No. 05042371
Patent Literature 3: International Publication No. 2009/145172
Patent Literature 4: Japanese Patent No. 04897054
Patent Literature 5: Japanese Patent No. 4853927
Patent Literature 6: Japanese Patent Laid-Open No. 10-160658

Non-Patent Literature

Non-Patent Literature 1: Tsutomu Horiuchi, Toru Miura, Yuzuru Iwasaki, Michiko Seyama, Suzuyo Inoue, Jun-ichi Takahashi, Tsuneyuki Haga and Emi Tamechika, "Passive fluidic chip composed of integrated vertical capillary tubes developed for on-site SPR immunoassay analysis targeting real samples.", Sensors 12, no. 6: (2012) 7095-7108

Non-Patent Literature 2: Glenn M. Walker and David J. Beebe, "A passive pumping method for microfluidic devices", Lab Chip, 2 (2002) 131-134

Non-Patent Literature 3: YuChang Kima, Seung-Hoon Kimb, Duckjong Kima, Sang-Jin Parka, Je-Kyun Parkb, "Plasma extraction in a capillary-driven microfluidic device using surfactant-added poly(dimethylsiloxane)", Sens. Actuators B, 145 (2010) 861-868

DISCLOSURE OF INVENTION

Problem to be Solved by the Invention

However, the above-described liquid feed control by a pump is difficult. This is because since the flow cell is very small, and the amount of the liquid to be fed is also very small, the pump needs to be delicately operated to attain a state in which the liquid stays in the channel and the delivery portion. In addition, since liquid feed control using a pump is also affected by the residual pressure in a pipe or the like, a time delay or water hammer occurs, and the operation is more complicated.

It is an object of the present invention to provide a flow cell and a liquid feed system capable of more easily controlling feed of a trace amount of liquid.

Means of Solution to the Problem

In order to solve the above-described problem, according to the present invention, there is provided a flow cell comprising a body, a concave portion formed in the body, and a channel formed inside the body and having one end open to an inner wall surface of the concave portion and the other end open to an outside of the body, wherein the channel causes a meniscus of a liquid introduced into the channel to apply a negative pressure to the liquid, and the concave portion causes a meniscus of a liquid introduced into the concave portion to apply, to the liquid, one of a positive pressure and a negative pressure whose absolute value is smaller than an absolute value of the negative pressure applied to the liquid introduced into the channel by the meniscus of the liquid.

A liquid feed system comprising a pump that generates a negative pressure, a flow cell including a body, a concave portion formed in the body, and a channel formed inside the body and having one end open to an inner wall surface of the concave portion and the other end open to an outside of the body, and a tube that connects the pump and the other end of the channel of the flow cell, wherein the channel causes a meniscus of a liquid introduced into the channel to apply a negative pressure to the liquid, the concave portion causes a meniscus of a liquid introduced into the concave portion to apply, to the liquid, one of a positive pressure and a negative pressure whose absolute value is smaller than an absolute value of the negative pressure applied to the liquid introduced into the channel by the meniscus of the liquid, and the pump generates a predetermined negative pressure whose absolute value is smaller than the absolute value of the negative pressure applied to the liquid introduced into the channel by the meniscus of the liquid and larger than the absolute value of the negative pressure applied to the liquid introduced into the concave portion by the meniscus of the liquid.

Effect of the Invention

According to the present invention, a predetermined negative pressure whose absolute value is smaller than that of the negative pressure applied to the liquid by the meniscus of the liquid introduced into the channel and larger than that of the negative pressure applied to the liquid by the meniscus of the liquid introduced into the concave portion is applied to the other end of the channel by the pump. When a liquid is supplied to the concave portion in this state, the liquid introduced into the concave portion moves to the channel because the negative pressure by the pump is larger than the negative pressure applied by the meniscus of the liquid introduced into the concave portion. When the liquid introduced into the concave portion wholly flows from the concave portion, the movement of the liquid introduced into the channel stops because the negative pressure applied by the meniscus of the liquid introduced into the channel is larger than the negative pressure by the pump. As a result, since the pump need not be operated delicately, it is possible to more easily control feed of a trace amount of liquid.

BEST MODE FOR CARRYING OUT THE INVENTION

An embodiment of the present invention will now be described in detail with reference to the accompanying drawings. Note that in this embodiment, an example in which the present invention is applied to an SPR measurement system will be described.

<Arrangement of SPR Measurement System>

Figure 1:
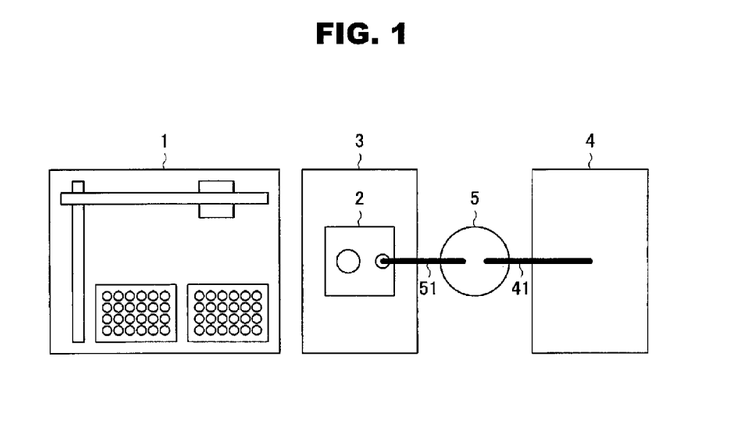
FIG. 1 is a plan view schematically showing the arrangement of an SPR measurement system.
Figure 2:
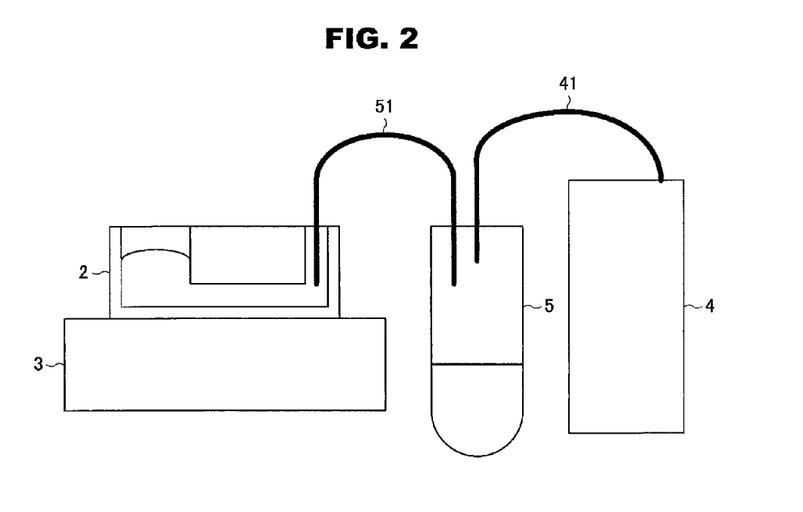
FIG. 2 is a front view schematically showing the arrangement of part of the SPR measurement system.

As shown in FIGS. 1 and 2, an SPR measurement system according to this embodiment includes a dispenser 1 that selectively supplies a specimen or reagent, a flow cell 2 to which the specimen or reagent is supplied from the dispenser 1, an SPR measurement device 3 that performs SPR measurement using the flow cell 2, a pump 4 that generates a predetermined negative pressure, and a pressure control vessel 5 that is provided between the flow cell 2 and the pump 4 and adjusts the pressure applied to the flow cell 2.

Figure 3:
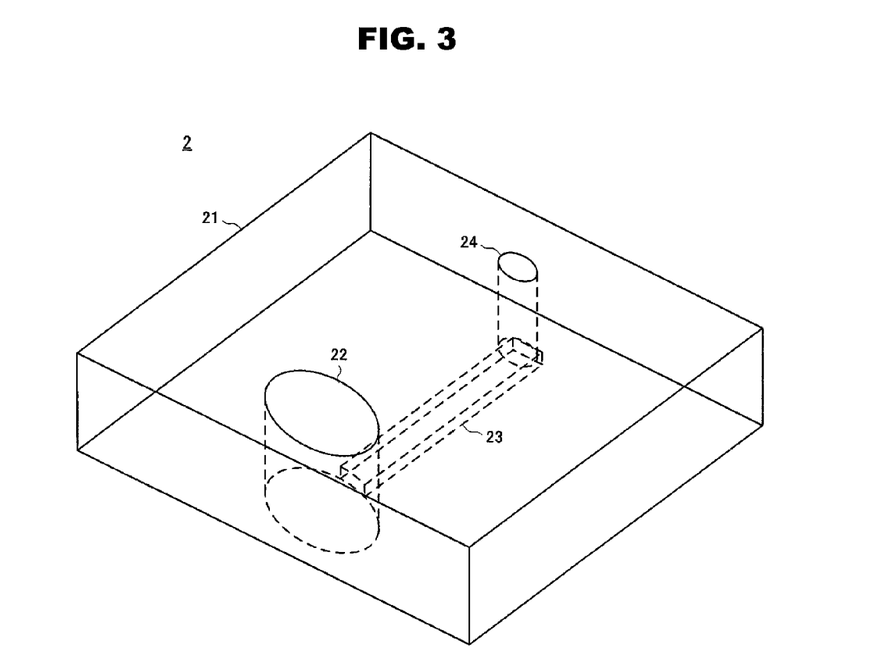
FIG. 3 is a perspective view schematically showing the arrangement of a flow cell according to an embodiment of the present invention.
Figure 4:
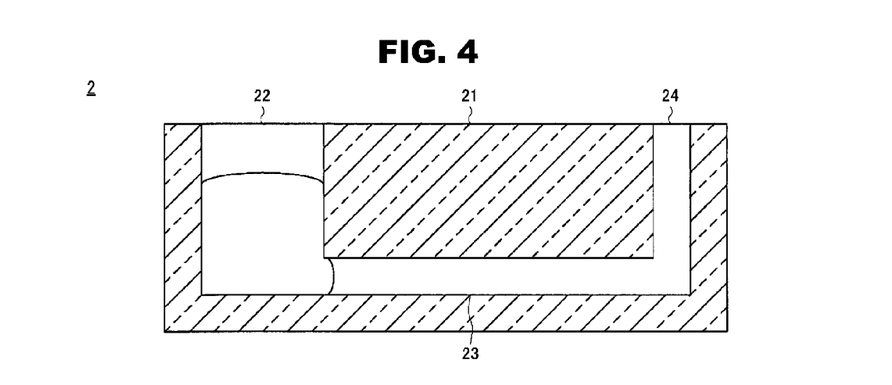
FIG. 4 is a sectional view schematically showing the arrangement of the main part of the flow cell according to the embodiment of the present invention.

As shown in FIGS. 3 and 4, the flow cell 2 includes a plate-shaped body 21 that is almost rectangular in a plan view, an introduction portion 22 that is made of a concave portion formed in the upper surface of the body 21, a channel 23 that is formed inside the body 21 and has one end connected to the lower end of the introduction portion 22, and a delivery portion 24 that is made of a concave portion formed in the body 21 and has the lower end connected to the other end of the channel 23. Note that the sectional area (to be referred to as "the sectional area of the introduction portion 22" hereinafter) in a direction perpendicular to a direction in which a liquid introduced into the introduction portion 22 flows is formed to be larger than the sectional area (to be referred to as "the sectional area of the channel 23" hereinafter) in a direction perpendicular to a direction in which a liquid introduced into the channel 23 flows.

The body 21 is made of, for example, a resin material.

The introduction portion 22 is a channel formed into a cylindrical shape (circular tube) with one end open to the upper surface of the body 21 and the other end closed. The inner wall surface of the introduction portion 22 is made of a material having hydrophobicity or a material having hydrophilicity to a liquid introduced into the flow cell 2. The pressure applied to the liquid by the meniscus of the liquid introduced from the opening of the introduction portion 22 is a positive pressure in a case in which the inner wall surface of the introduction portion 22 is hydrophobic or a negative pressure in a case in which the inner wall surface is hydrophilic. In addition, the sectional area of the introduction portion 22 is formed to be larger than the sectional area of the channel 23. Hence, the introduction portion 22 is formed such that the absolute value of the negative pressure applied to the liquid by the liquid introduced into the introduction portion 22 becomes smaller than the absolute value of the negative pressure applied to the liquid by the liquid introduced into the channel 23.

The positive pressure applied to the liquid by the meniscus means a force that applies a pressure, in the discharge direction, to the introduction side portion of the liquid introduced into the introduction portion 22 and the channel 23, in other words, a force that applies a pressure to the gas-liquid interface of the liquid in the direction toward the liquid. On the other hand, the negative pressure applied to the liquid by the meniscus means a force that applies a pressure, in the sucking direction, to the introduction side portion of the liquid introduced into the introduction portion 22 and the channel 23, in other words, a force that applies a pressure to the gas-liquid interface of the liquid in the direction toward the gas.

A pressure Pr by the meniscus formed in the cylindrical introduction portion 22 is given by equation (1) below. In equation (1), r is the radius of the introduction portion 22, θ is the contact angle to the inner wall surface of the introduction portion 22, and γ is the surface tension coefficient of the liquid introduced into the introduction portion 22.

$$Pr = -(2\gamma/r)\cos\theta \quad (1)$$

For example, when water ($\gamma=72.75\times10^{-3}$ [N/s]) is supplied to the introduction portion 22, the radius r of the introduction portion 22 is 3 [mm], and the inner wall surface of the introduction portion 22 is hydrophilic (contact angle $\theta=60[°]$), the pressure Pr is −24.25 [Pa]. This means that a negative pressure of 24.25 [Pa] is applied to the water introduced into the introduction portion 22 by the meniscus formed in the introduction portion 22, and to move the water in the direction of the channel 23, the water needs to be sucked to the side of the channel 23, that is, by the pump 4 with a negative pressure of 24.25 [Pa] or more.

The channel 23 is a tube having a rectangular section and extending in a direction parallel to the upper surface of the body 21. One end of the channel 23 opens to the inner wall surface at the bottom of the introduction portion 22, and the other end opens to the inner wall surface at the bottom of the delivery portion 24. The inner wall surface of the channel 23 is formed such that the meniscus of the liquid introduced into the channel 23 applys a negative pressure. More specifically, the inner wall surface of the channel 23 is made of a material having hydrophilicity to the liquid supplied to the flow cell 2. Hence, when the liquid is introduced into the hydrophilic channel 23 and the meniscus is formed, a negative pressure is applied to the liquid by the meniscus.

A pressure Pc applied by the meniscus formed in the channel 23 having an almost rectangular section can be given by equation (2). In equation (2), d is the thickness of the channel 23, w is the width of the channel 23, $\theta t$ is the contact angle of the upper surface of the channel 23, $\theta b$ is the contact angle of the bottom surface of the channel 23, $\theta l$ is the contact angle of the left surface of the channel 23, and $\theta r$ is the contact angle of the right surface of the channel 23.

$$Pc=-\gamma\{(\cos\theta l/d)+(\cos\theta b/d)+(\cos\theta l/w)+(\cos\theta r/w)\} \quad (2)$$

If the surfaces have the same contact angle $\theta$, equation (2) can be rewritten to $$Pc=-2\gamma\cos\theta\{(l/d)+)l/w)\} \quad (3)$$

For example, when water ($\gamma=72.75\times10^{-3}$ [N/s]) is supplied to the channel 23, the thickness of the channel 23 is 0.075 [mm], the width is 1 [mm], and the inner wall surface of the channel 23 is hydrophilic (contact angle $\theta=60[°]$), the pressure Pc is −1042.75 [Pa]. This means that a negative pressure of 1042.75 [Pa] is applied to the water introduced into the channel 23 by the meniscus formed in the channel 23, and to move the water in the direction of the delivery portion 24, the water needs to be sucked to the side of the delivery portion 24, that is, by the pump 4 with a negative pressure of 1042.75 [Pa] or more.

The delivery portion 24 is a channel formed into a cylindrical shape (circular tube) with one end open to the upper surface of the body 21 and the other end closed. The other end of a tube 51 whose one end is connected to the pressure control vessel 5 is connected to the delivery portion 24.

Note that in this embodiment, when the flow cell 2 is used for SPR measurement, at least part of the bottom surface of the channel 23 is provided with a detection portion (not shown) made of Au or the like.

A method of manufacturing the flow cell 2 will be described later.

The SPR measurement device 3 is a device that performs measurement by the SPR method. In this embodiment, measurement is performed for the liquid that flows in the channel 23 of the flow cell 2 arranged on the SPR measurement device 3.

The pump 4 is a pump that generates a predetermined negative pressure, and is connected to the delivery portion 24 of the flow cell 2 via a tube 41, the pressure control vessel 5, and the tube 51. The predetermined negative pressure has a predetermined value whose absolute value is smaller than that of the negative pressure applied to the liquid by the meniscus of the liquid introduced into the channel 23 with the hydrophilic inner wall surface and larger than that of the negative pressure applied to the liquid by the meniscus of the liquid introduced into the introduction portion 22 with the hydrophilic inner wall surface. Note that even when a positive pressure is applied to the liquid by the meniscus formed in the introduction portion 22 by the liquid introduced into the introduction portion 22 with the hydrophobic inner wall surface, the value of the negative pressure of the pump 4 is set such that the absolute value becomes smaller than that of the negative pressure applied to the liquid by the meniscus of the liquid introduced into the channel 23.

The negative pressure generated by the pump 4 is the same "negative pressure" as the negative pressure applied to the liquid by the meniscus formed in the introduction portion 22 or the channel 23 by the liquid introduced into there, but the direction of applying the pressure is different. That is, the negative pressure generated by the pump 4 is a pressure in a direction in which the liquid introduced into the introduction portion 22 is sucked toward the channel 23. On the other hand, the negative pressure by the meniscus formed in the introduction portion 22 or the channel 23 is, in the case of the liquid in the channel 23, a pressure in a direction in which the liquid is sucked toward the introduction portion 22.

The pressure control vessel 5 is formed from a tubular hollow vessel whose upper end is connected to the other end of the tube 41 and one end of the tube 51 whose other end is connected to the delivery portion 24 of the flow cell 2. The pressure control vessel 5 is configured to cancel a pressure difference generated in the liquid in the tube 51 and normally operate the pump 4.

<Method of Manufacturing Flow Cell>

An example of a method of manufacturing the flow cell 2 according to this embodiment will be described next with reference to FIGS. 5A to 5G.

Figure 5A:
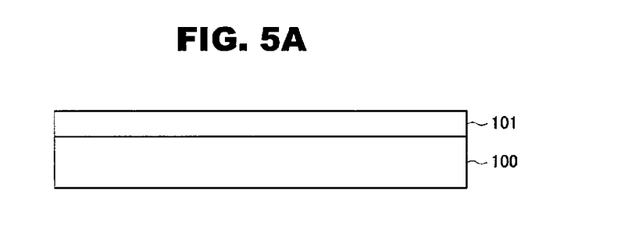
FIG. 5A is a sectional view for explaining a method of manufacturing the flow cell according to the embodiment of the present invention.

First, to make a mold corresponding to the shape of the channel 23, as shown in FIG. 5A, a silicon wafer 100 is prepared, and a resist 101 is formed on the silicon wafer 100. For example, as the silicon wafer 100, a silicon wafer subjected to a sulfuric acid/hydrogen peroxide mixture treatment, that is, so-called piranha cleaning for 30 min and dried at 200° C. for 20 min before application of the resist 101 is prepared. As the resist 101, a thick resist SU8 is used, and this is applied to the upper surface of the silicon wafer 100 by spin coating.

Figure 5B:
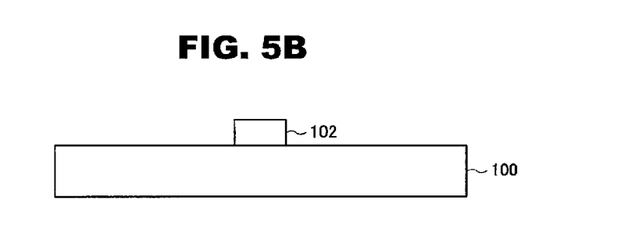
FIG. 5B is a sectional view for explaining a method of manufacturing the flow cell according to the embodiment of the present invention.

Next, as shown in FIG. 5B, a mold 102 corresponding to the shape of the channel 23 is formed on the silicon wafer 100 by photolithography. For example, the silicon wafer 100 to which the resist 101 is applied as shown in FIG. 5A is baked sequentially at 65° C. for 30 min and at 95° C. for 270 min, exposed by an aligner, and then post-baked at 95° C. for 90 min. The silicon wafer 100 is developed using a developer for SU8 and rinsed by isopropyl alcohol acetone. An outer frame is mounted on the periphery to complete the mold. Note that in this embodiment, the mold in the portion corresponding to the channel 23 is 0.075 [mm] thick, 1 [mm] wide, and 9 [mm] long.

Figure 5C:
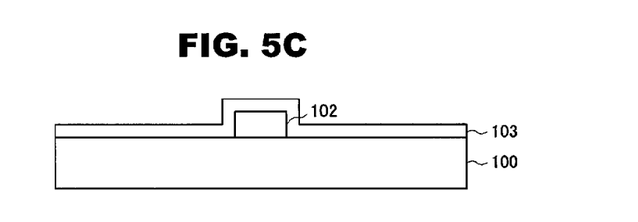
FIG. 5C is a sectional view for explaining a method of manufacturing the flow cell according to the embodiment of the present invention.

After the mold 102 is made, a hydrophilic PDMS 103 is applied to the upper surface of the silicon wafer 100 with the mold 102, as shown in FIG. 5C.

For example, as the hydrophilic PDMS 103, hydrophilic PDMS obtained by adding 1 wt % of polyether-modified silicone (trisiloxane ethoxylate) (SILWET L-77) to hydrophobic PDMS before hardening and performing vacuum degassing for the resultant substance can be used. The hydrophobic PDMS before hardening is obtained by mixing a PDMS base (SYLGARD 184) and a polymerization initiator at a ratio of 10:1 and performing vacuum degassing for the resultant substance. To apply the hydrophilic PDMS 103, a method using a microdispenser, a brush, or the like or a printing technique such as intaglio printing, relief printing, lithography, or mimeograph is used.

Figure 5D:
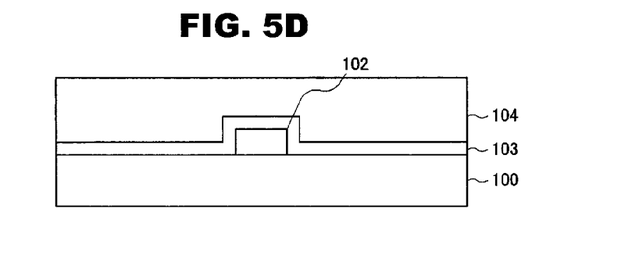
FIG. 5D is a sectional view for explaining a method of manufacturing the flow cell according to the embodiment of the present invention.

After the hydrophilic PDMS 103 is applied, a hydrophobic PDMS 104 is formed on the hydrophilic PDMS 103, as shown in FIG. 5D.

For example, the hydrophobic PDMS 104 is evenly formed to a thickness of about 3 [mm] on the hydrophilic PDMS 103 and then heated for 120 min to harden.

Figure 5E:
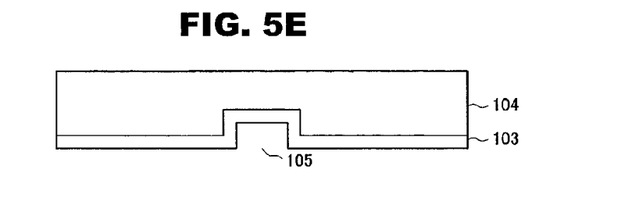
FIG. 5E is a sectional view for explaining a method of manufacturing the flow cell according to the embodiment of the present invention.

When the hydrophobic PDMS 104 is hardened, the silicon wafer 100 and the mold 102 are separated from the hydrophilic PDMS 103 in which a groove 105 corresponding to the channel 23 is formed and the hydrophobic PDMS 104 provided on the hydrophilic PDMS 103, as shown in FIG. 5E.

Figure 5F:
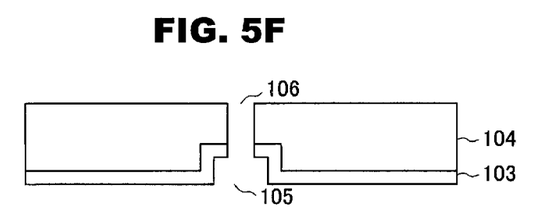
FIG. 5F is a sectional view for explaining a method of manufacturing the flow cell according to the embodiment of the present invention.

Subsequently, as shown in FIG. 5F, through holes 106 that make the groove 105 communicate with the upper surface of the hydrophobic PDMS 104 are formed at both ends of the groove 105. The through holes 106 correspond to the introduction portion 22 and the delivery portion 24. For example, the through hole 106 corresponding to the introduction portion 22 is formed to a diameter of 3 [mm], and the through hole 106 corresponding to the delivery portion 24 is formed to a diameter of 1.5 [mm].

Figure 5G:
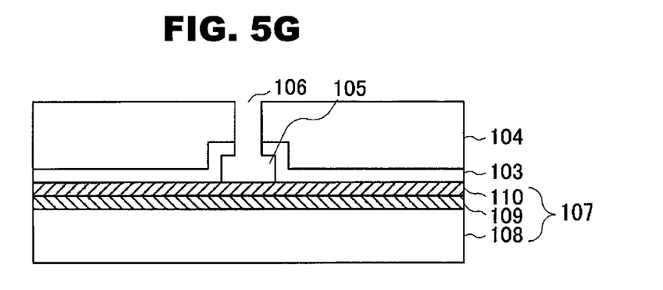
FIG. 5G is a sectional view for explaining a method of manufacturing the flow cell according to the embodiment of the present invention.

When the through holes 106 are formed, an SPR substrate 107 is prepared, and the bottom surface of the hydrophilic PDMS 103 is bonded to the upper surface of the SPR substrate 107, as shown in FIG. 5G. The flow cell 2 is thus completed.

The SPR substrate 107 is a substrate to be placed on the SPR measurement device 3 and is formed by sequentially sputtering a thin titanium film 109 and a thin gold film 110 on a BK7 glass substrate 108. For example, the bonding is done by activating the bottom surface of the hydrophilic PDMS 103 and the upper surface of the SPR substrate 107 by reactive ion etching (power: 70 [W], oxygen partial pressure: 10 [Pa], flow rate: 100 [sccm], 5 sec) in an oxygen atmosphere and bonding these surfaces.

In the created flow cell 2, the inner wall surface of the channel 23 is hydrophilic because it is formed from the hydrophilic PDMS 103. Hence, when a meniscus is formed in the liquid flowing into the channel 23, a negative pressure is applied to the liquid by the meniscus.

On the other hand, the inner wall surfaces of the introduction portion 22 and the delivery portion 24 are hydrophobic because they are formed from the hydrophobic PDMS 104. Hence, when a meniscus is formed in the liquid flowing into the introduction portion 22 or the delivery portion 24, a positive pressure is applied to the liquid by the meniscus.

<Measurement Operation by SPR Measurement System>

A measurement operation by the SPR measurement system including the flow cell 2 created by the manufacturing method will be described next with reference to FIGS. 6A to 6D.

Note that in this embodiment, an example in which pure water α and a phosphate buffer β are alternately fed to the flow cell 2, and their flow velocities are measured will be described. For example, an automatic dispenser PIPET-MASTER-2005 available from Musashi Engineering can be used as the dispenser 1, smart SPR available from NTT-AT can be used as the SPR measurement device, and a pump MFCS-VAC available from Fluigent can be used as the pump 4.

Figure 6A:
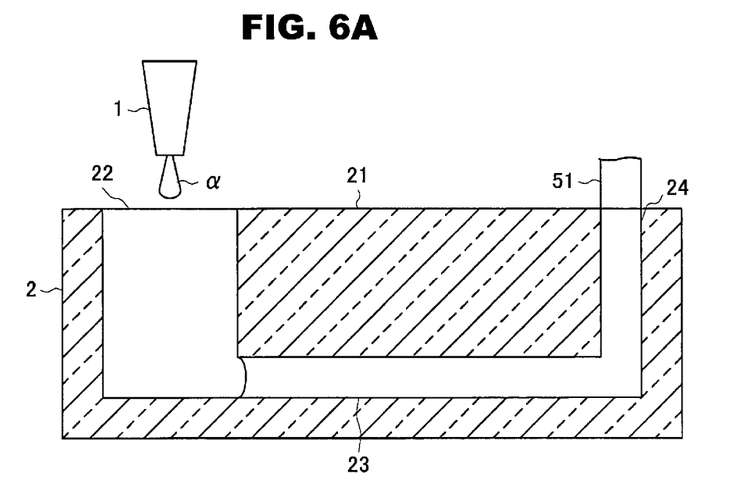
FIG. 6A is a view for explaining a measurement operation by the SPR measurement system.

First, priming water is injected from the opening of the introduction portion 22 in advance to attain a state in which the channel 23 and the delivery portion 24 are filled with the water. After this state is attained, the pressure of the pump 4 is set to a predetermined negative pressure, and the pure water α is introduced by the dispenser 1 into the opening of the introduction portion 22 of the flow cell 2, as shown in FIG. 6A.

In this embodiment, the pressure of the pump 4 is set to −100 [Pa].

Figure 6B:
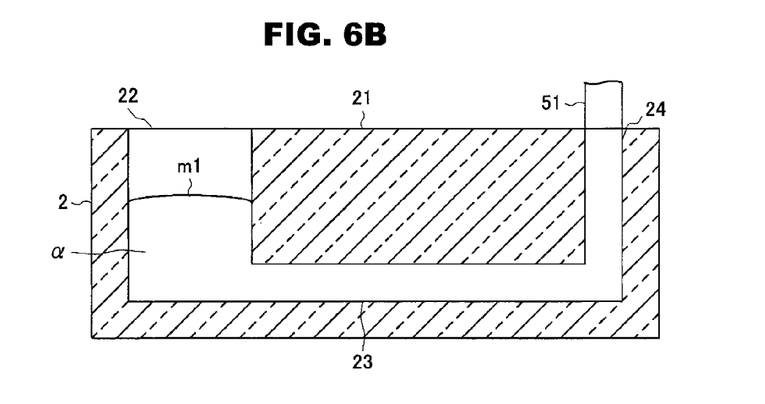
FIG. 6B is a view for explaining a measurement operation by the SPR measurement system.

In addition, 0.01 [ml] of pure water α is introduced by the dispenser 1 into the opening of the introduction portion 22 of the flow cell 2. In this embodiment, since the capacity of the introduction portion 22 is about 0.02 [ml], the pure water α does not overflow from the opening of the introduction portion 22, as shown in FIG. 6B.

At this time, the inner wall surface of the introduction portion 22 is formed from the hydrophobic PDMS 104. Hence, a meniscus m1 formed by the liquid injected into the introduction portion 22 has a convex shape and applies, to the liquid, a positive pressure, that is, a force to move the liquid toward the channel 23.

In this way, the pure water α injected into the introduction portion 22 is moved from the introduction portion 22 to the channel 23 by the pressure (positive pressure) applied by the meniscus formed in the introduction portion 22 and the pressure (negative pressure) from the pump 4. The pure water α moved to the channel 23 passes through the channel 23 and then through the delivery portion 24, and is then introduced from the tube 51 to the pressure control vessel 5.

Figure 6C:
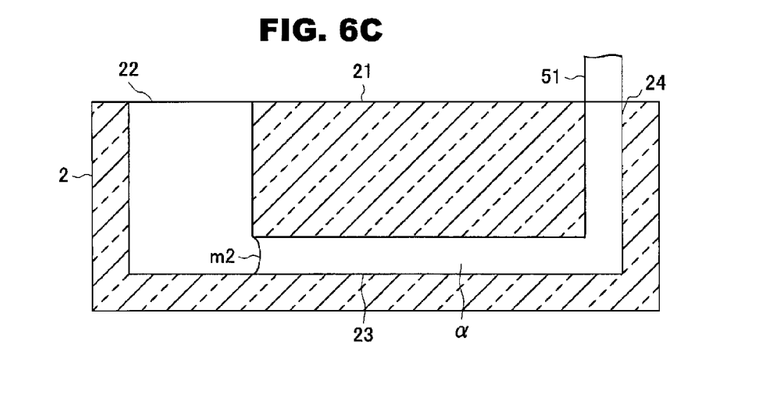
FIG. 6C is a view for explaining a measurement operation by the SPR measurement system.

When the pure water α injected into the introduction portion 22 wholly flows into the channel 23, and a meniscus m2 is formed near the end of the channel 23 on the side of the introduction portion 22, the movement of the pure water α stops, as shown in FIG. 6C. This is because the pressure (negative pressure) by the meniscus m2 formed in the channel 23 is larger than the pressure (negative pressure) by the pump 4.

At this time, both the pressure by the meniscus m2 formed in the channel 23 and the pressure by the pump 4 are negative, but the sucking directions are different, as described above. That is, the meniscus m2 sucks the liquid in the channel 23 in the direction toward the introduction portion 22, and the pump 4 sucks the liquid in the channel 23 in the direction toward the delivery portion 24. Hence, since the pressure by the meniscus m2 is larger than the pressure by the pump 4, the movement of the liquid (pure water α) stops.

Figure 6D:
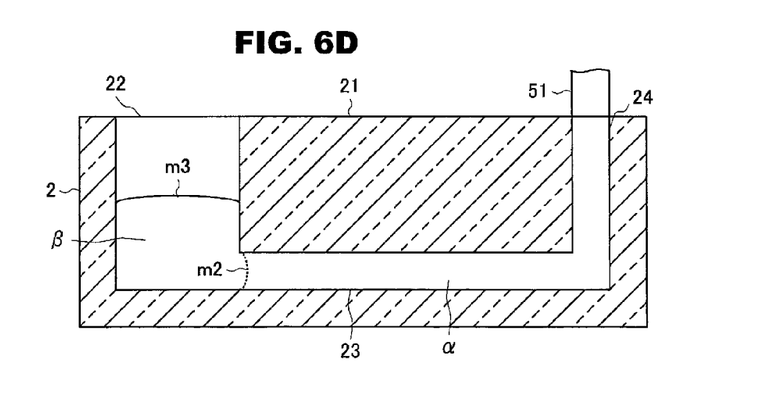
FIG. 6D is a view for explaining a measurement operation by the SPR measurement system.

When the movement of the pure water α stops, the phosphate buffer β is introduced by the dispenser 1 into the opening of the introduction portion 22 of the flow cell 2, as shown in FIG. 6D. In this embodiment, 0.01 [ml] of phosphate buffer β is introduced.

Then, the meniscus m2 formed by the pure water α at the end of the channel 23 on the side of the introduction portion 22 disappears along with the introduction of the phosphate buffer β, and the negative pressure applied by the meniscus m2 is lost. On the other hand, a meniscus m3 is formed in the introduction portion 22 by the phosphate buffer β. Accordingly, the phosphate buffer β injected into the introduction portion 22 is moved from the introduction portion 22 to the channel 23 by the pressure (positive pressure) applied by the meniscus m3 and the pressure (negative pressure) from the pump 4. In this case, since the inner wall surface of the introduction portion 22 is hydrophobic, the flow velocity of the phosphate buffer β increases as compared to a case in which the inner wall surface is hydrophilic, and the dirt of the phosphate buffer β hardly adheres to the inner wall surface.

At this time, since the refractive indices of the pure water α and the phosphate buffer β largely differ, the boundary between the liquids can be observed by the SPR measurement device 3. The SPR measurement device 3 used in this embodiment has a 3.5-[mm] observation region in the flow direction of the channel 23. Hence, the flow velocity of the liquid can be obtained by measuring the time the boundary between the liquids passes across the observation region.

Like the pure water α, the phosphate buffer β that has wholly flowed from the introduction portion 22 stops at the end of the channel 23 on the side of the introduction portion 22. As described above, when a liquid is introduced into the introduction portion 22, the liquid automatically moves to the channel 23. When the liquid wholly flows from the introduction portion 22, the movement automatically stops. It is therefore possible to control feed of a trace amount of liquid only by supplying the liquid to the introduction portion 22 without delicately controlling the pump as before. It is also possible to attain a state in which a liquid stays in the channel 23 and the delivery portion 24 without delicately controlling the pump as before. Hence, time to resupply the priming water can be saved.

By subsequently injecting the pure water α and the phosphate buffer β into the introduction portion 22 alternately in this order, the pure water α and the phosphate buffer β can repetitively be measured.

Figure 7:
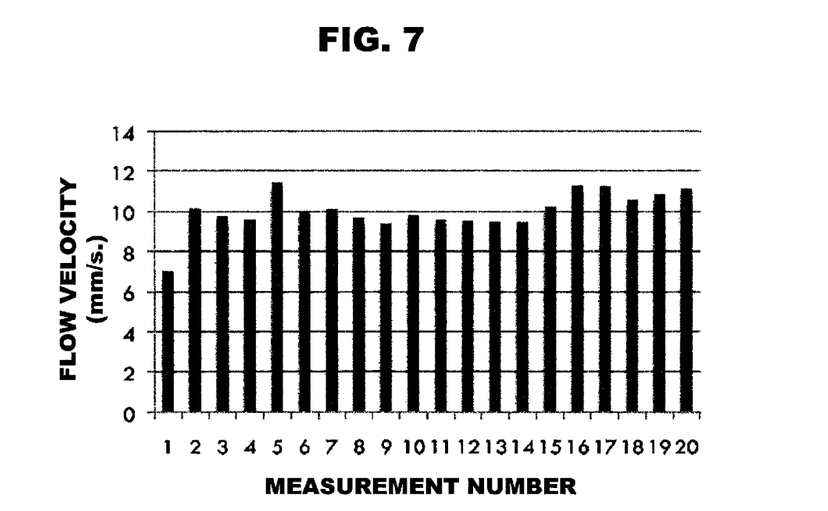
FIG. 7 is a graph showing a flow velocity measurement result obtained when pure water and a phosphate buffer are alternately supplied.

FIG. 7 shows a measurement result obtained by alternately supplying the pure water α and the phosphate buffer β to the introduction portion 22 and measuring the moving speed of the boundary repetitively (20 times) in accordance with the above-described procedure. As shown in FIG. 7, the moving speed of the boundary, that is, the flow velocity of the liquid flowing through the channel 23 exhibits an almost constant value.

In this way, it is possible to feed a liquid to the channel 23 only by supplying the liquid to the introduction portion 22 without controlling feed of a trace amount of fluid using a pump as before.

<Blood Coagulation Measurement>

Blood coagulation measurement according to this embodiment will be described next.

Coagulation factors responsible for a hemostatic action include prothrombin. To evaluate the coagulation capability of prothrombin, a prothrombin time is used. The prothrombin time is measured and used as an indicator in a liver function test (cirrhosis or liver cancer) or to determine an anticoagulant dose at the time of surgery of a myocardial infarction, brain infarction, or the like. Conventionally, a time until a plasma is coagulated by a reagent is measured. However, when coagulation measurement is conducted in a flow cell, the channel clogs, and repetitive measurement cannot be performed. In this embodiment, however, measurement is performed in accordance with the following procedure, thereby performing repetitive measurement.

First, required amounts of plasma (coagulation activation ratio: 100%), coagulation activator, channel cleaning fluid, and pure water are prepared in the reservoirs of the dispenser 1 in advance. Required amounts of channel cleaner and pure water are sequentially introduced into the opening of the introduction portion 22 of the flow cell 2. The coagulation activator is supplied and kept stopped in the channel 23. In this state, the plasma is introduced from the introduction portion 22, and the SPR measurement device 3 starts measurement. A coagulation reaction starts in the interface (the connection portion between the introduction portion 22 and the channel 23) between the plasma and the coagulation activator in the channel 23. Since the coagulation activator starts flowing in the channel 23 at the same time as the introduction of the plasma, the channel 23 does not clog.

At this time, the SPR measurement device 3 can measure the transit time (flow velocity) of the interface between the coagulation activator and the plasma. When the same operation as described above is performed again from the introduction of the channel cleaner, repetitive measurement can be performed.

Figure 8:
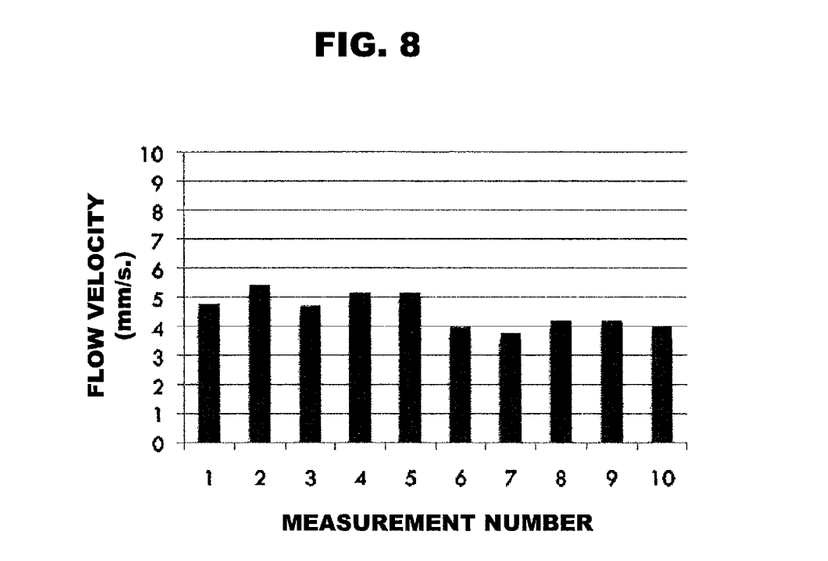
FIG. 8 is a graph showing a measurement result of blood coagulation measurement.

FIG. 8 shows a measurement result obtained by performing blood coagulation measurement repetitively (10 times) in accordance with the above-described procedure. As shown in FIG. 8, the flow velocity is about 4.5 mm/s], exhibiting an almost constant value.

Figure 9:
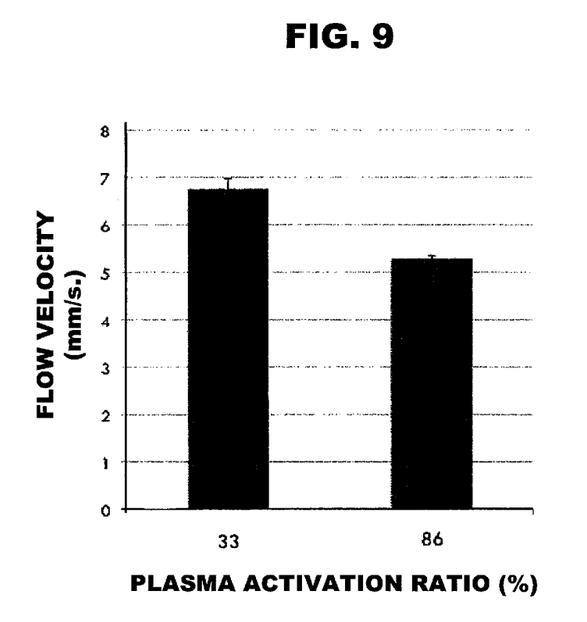
FIG. 9 is a graph showing a measurement result of blood coagulation measurement.

FIG. 9 shows a result obtained by performing the same measurement using plasmas of different coagulation activation ratios and comparing the results. In a plasma whose coagulation activation ratio was 33%, the flow velocity was 6.6 [mm/s]. In a plasma whose coagulation activation ratio was 86%, the flow velocity was 5.4 [mm/s]. As can be seen from comparison with the measurement result shown in FIG. 8 in which the coagulation activation ratio was 100%, the plasma with a high coagulation activation ratio readily coagulates, its flow velocity is measured low, and this is an effective indicator in blood coagulation capability measurement.

As described above, according to this embodiment, a predetermined negative pressure whose absolute value is smaller than that of the negative pressure applied to the liquid by the meniscus of the liquid introduced into the channel 23 and larger than that of the negative pressure applied to the liquid by the meniscus of the liquid introduced into the introduction portion 22 is applied to the other end of the channel 23 by the pump 4. When a liquid is supplied to the introduction portion 22 in this state, the liquid introduced into the introduction portion 22 moves to the channel 23 because the negative pressure by the pump 4 is larger than the negative pressure applied by the meniscus of the liquid introduced into the introduction portion 22. When the liquid introduced into the introduction portion 22 wholly flows from the introduction portion 22, the movement of the liquid introduced into the channel 23 stops because the negative pressure applied by the meniscus of the liquid introduced into the channel 23 is larger than the negative pressure by the pump 4. As a result, since the pump 4 need not be operated delicately, it is possible to more easily control feed of a trace amount of liquid.

Note that in this embodiment, an example in which the present invention is applied to an SPR measurement system has been described. However, the present invention is applicable to various kinds of systems as long as the systems measure a trace amount of liquid fed in the channel of the flow cell.

Additionally, in this embodiment, an example in which the entire channel 23 is hydrophilic has been described. However, at least the portion near the connection portion to the introduction portion 22 needs to be hydrophilic.

Furthermore, in this embodiment, a case in which the inner wall surface of the introduction portion 22 is formed from the hydrophobic PDMS 104, and the inner wall surface of the channel 23 is formed from the hydrophilic PDMS 103 has been described. However, the present invention is not limited to this, and both the inner wall surface of the introduction portion 22 and that of the channel 23 may be formed from the hydrophilic PDMS 103.

In this case, since the concave meniscus m2 formed by the pure water α at the end of the channel 23 on the side of the introduction portion 22 disappears due to the phosphate buffer β supplied from the introduction portion 22, the negative pressure generated in the channel 23 by the meniscus m2 (see FIG. 6C) toward the introduction portion 22 is lost, and simultaneously, a new concave meniscus is formed in the hydrophilic introduction portion 22 by the phosphate buffer β. Since the sectional area of the introduction portion 22 is larger than the sectional area of the channel 23, the force (negative pressure) generated by the new meniscus formed in the introduction portion 22 is smaller than the force (negative pressure) generated by the meniscus m2 formed in the channel 23. Hence, since the pressure (negative pressure) from the pump 4 is larger than the force (negative pressure) generated by the new meniscus in the introduction portion 22, the phosphate buffer β injected into the introduction portion 22 moves from the introduction portion 22 to the channel 23.

Additionally, in this embodiment, a case in which the sectional area of the introduction portion 22 is formed to be larger than the sectional area of the channel 23 has been described. However, the present invention is not limited to this. If the inner wall surface of the introduction portion 22 is hydrophobic, the convex meniscus m3 is formed in the introduction portion 22. Hence, the sectional area of the introduction portion 22 may be formed to be smaller than or equal to the sectional area of the channel 23.

INDUSTRIAL APPLICABILITY

The present invention is applicable to various kinds of devices and methods using a flow cell.

EXPLANATION OF THE REFERENCE NUMERALS AND SIGNS

1 . . . dispenser, 2 . . . flow cell, 3 . . . SPR measurement device, 4 . . . pump, 5 . . . pressure control vessel, 21 . . . body, 22 . . . introduction portion, 23 . . . channel, 24 . . . delivery portion, 51 . . . tube

The invention claimed is:
1. A liquid feed system comprising:
a pump that generates a negative pressure;
a flow cell including a body, a concave portion formed in the body, and a channel formed inside the body and having one end open to an inner wall surface of the concave portion and the other end open to an outside of the body; and
a tube that connects the pump and the other end of the channel of the flow cell,
wherein the channel causes a meniscus of a liquid introduced into the channel to apply a negative pressure to the liquid,
the concave portion causes a meniscus of a liquid introduced into the concave portion to apply, to the liquid, one of a positive pressure and a negative pressure whose absolute value is smaller than an absolute value of the negative pressure applied to the liquid introduced into the channel by the meniscus of the liquid, and
the pump generates a predetermined negative pressure whose absolute value is smaller than the absolute value of the negative pressure applied to the liquid introduced into the channel by the meniscus of the liquid and larger than the absolute value of the negative pressure applied to the liquid introduced into the concave portion by the meniscus of the liquid.

* * * * *